United States Patent
Ropiak

Patent Number: 5,860,954
Date of Patent: Jan. 19, 1999

[54] MULTIPLE HOLE DRUG DELIVERY BALLOON

[75] Inventor: Susan M. Ropiak, Hanscom AFB, Mass.

[73] Assignee: Boston Scientific Corporation, Natick, Mass.

[21] Appl. No.: 939,461

[22] Filed: Sep. 29, 1997

Related U.S. Application Data

[60] Continuation of Ser. No. 636,606, Apr. 23, 1996, abandoned, which is a division of Ser. No. 414,650, Mar. 31, 1995, abandoned.

[51] Int. Cl.⁶ ................................ A61M 29/00
[52] U.S. Cl. ............................. 604/96; 606/194
[58] Field of Search ................. 604/96, 101, 102; 606/194

[56] References Cited

U.S. PATENT DOCUMENTS

| | | | |
|---|---|---|---|
| 4,693,243 | 9/1987 | Buras | 128/207 |
| 4,821,722 | 4/1989 | Miller et al. | |
| 4,994,033 | 2/1991 | Shockey et al. | 604/101 |
| 5,049,132 | 9/1991 | Shaffer et al. | 604/101 |
| 5,207,644 | 5/1993 | Strecker | 604/93 |
| 5,213,576 | 5/1993 | Abiuso et al. | 604/96 |
| 5,219,335 | 6/1993 | Willard et al. | 604/164 |
| 5,254,089 | 10/1993 | Wang | 604/96 |
| 5,295,962 | 3/1994 | Crocker et al. | 604/101 |
| 5,318,531 | 6/1994 | Leone | 604/96 |
| 5,320,604 | 6/1994 | Walker et al. | 604/96 |
| 5,328,471 | 7/1994 | Slepian | 604/101 |
| 5,336,178 | 8/1994 | Kaplan et al. | |
| 5,514,092 | 5/1996 | Forman et al. | 604/101 |

*Primary Examiner*—Mark Bockelman
*Attorney, Agent, or Firm*—Pearson & Pearson

[57] ABSTRACT

An inflatable medical device for delivery of medication to an organ in the body having a multi-lumen catheter and a hollow, inflatable channel-like medication deliverable balloon at the distal end of the catheter. A plurality of conduits extend along the balloon between the walls of the balloon for delivery of medications. Each conduit includes an array of closely spaced apertures for allowing medications in the conduits to transfer out of the conduits into a surrounding vessel after the balloon is inflated.

4 Claims, 3 Drawing Sheets

1

MULTIPLE HOLE DRUG DELIVERY BALLOON

This application is a continuation of U.S. patent application Ser. No. 08/636,606 filed Apr. 23, 1996 now abandoned which is a division of U.S. patent application 08/414,650, filed Mar. 31, 1995 now abandoned.

BACKGROUND OF THE INVENTION

1. Field of the Invention

This invention generally relates to balloon catheters for forcibly expanding a coronary artery and for dispensing medications. More particularly this invention is directed to a balloon catheter capable of delivering medications and to a method of manufacturing such a balloon catheter.

2. Description of Related Art

Balloon catheters for expanding atherosclerotic lesions or stenosises are well known in the heart. Such devices include inflatable balloons disposed at the end of multi-lumen catheter shafts. A pressurizing fluid forced into the balloon through an inflation lumen expands the balloon into the surface of an artery to enlarge its cross section.

U.S. Pat. No. 4,994,033 to Shockey et al. discloses a variation on a balloon catheter that is designed to apply a liquid medicament or other substance to a stenotic lesion as the blood vessel is undergoing dilatation to facilitate the restoration and long-term maintenance of patency to the blood vessel. This particular catheter includes three concentrically arranged flexible plastic tubes and a pair of concentrically arranged expansion members located at the distal end of the tubes. The space between the outer wall of the inner tube and the inner wall of the intermediate tube is in fluid communication with the interior of the first expander member. The second space between the outer wall of the intermediate tube and the inner wall of the outer tube is in fluid communication with the interior of the second expander member. A plurality of minute holes are formed through the second expander member to permit the liquid medicament to be ejected from the second expander member while an inflation fluid is introduced into the lumen of the intermediate tube.

Essentially, the Shockey et al. patent discloses two concentric balloons with an annular chamber formed between the balloons for receiving a medication that then disperses through the outer balloon through a series of holes. Other devices for performing these functions also exist. For example, U.S. Pat. No. 5,207,644 to Strecker discloses a similar device in the form of an implantable infusion chamber; and U.S. Pat. No. 5,320,604 to Walker et al. discloses a pair of expander balloons spaced apart on opposite sides of a waist portion at the distal end of a catheter in which the waist portion includes an infusion section with a perforation in communication with a drug delivery lumen. U.S. Pat. No. 4,693,243 to Buras discloses a flexible, non-collapsible conduit system for directly administering topical anesthesia in which the conduit system is separately positioned about a cuffed endotracheal tube for a direct topical application of additional substances to tissues of the larynx. U.S. Pat. No. 5,295,962 to Crocker et al. discloses a drug delivery and dilatation catheter that includes a inflation balloon disposed about a catheter and a perforated drug delivery balloon disposed concentrically about the inflation balloon. The drug delivery balloon contains a plurality of delivery ports over some or all of the surface of the delivery balloon or alternatively comprises a permeable material. U.S. Pat. No. 5,049,132 to Shaffer et al. also discloses a balloon catheter with concentric balloons. In this patent the outer balloon has apertures or slits that permit liquid flow outwardly through the balloon.

Increasing the pressure applied at the proximal end of many of the foregoing balloon catheters for administering a medicant increases the flow rate through the apertures. With sufficient pressure, "jetting" occurs whereby a relatively high-velocity stream emerges from the balloon with enough momentum to damage surrounding tissue. As one solution to this problem U.S. Pat. No. 5,213,576 to Abiuso et al. discloses two concentric balloons in which a medicament is directed into a central balloon and escapes through apertures in the inner balloon that are offset from apertures in an outer balloon. Each of the apertures or ports is sized to permit medication delivered through the lumen to pass outwardly through the perforations of both balloons, but the offset nature of the apertures prevents jetting.

U.S. Pat. No. 5,318,531 to Leone discloses an alternative infusion balloon catheter in which a balloon carries a plurality of holes sized to permit medication to be delivered through a lumen to pass outwardly through the holes. The balloon also carries on an outer surface a substantially hydrophilic, tubular, microporous membrane that covers the holes to break up streams of flowing medication.

More recently, an alternative balloon catheter, called a channel balloon, has been developed for the treatment of vascular disease including the delivery of medication to a site. One embodiment of such a balloon is shown in U.S. Pat. No. 5,254,089 to Wang. This channel balloon comprises a hollow, inflatable, extruded medication delivery balloon at the distal end of the catheter. Like other balloons, the interior of the channel balloon is in fluid flow relationship with one of several catheter lumens to enable the balloon to be inflated. In this particular structure, however, the balloon has inner and outer walls and angularly spaced radial webs that define an array of longitudinally extending conduits between the walls of the balloon. Another lumen in the catheter shaft delivers medication to these conduits, and the walls of the balloon have a single aperture for allowing the release of the medication from each conduit.

In the particular embodiment shown in the Wang patent, each conduit has a single port formed by inflating both the balloon and the conduits with air and then pricking each conduit wall lightly with a pin until it deflates. It is also suggested that the conduits could be pierced with laser irradiation. Apertures in the range from 0.0025 mm to 2.5 mm are suggested as potential aperture sizes depending upon the viscosity of the medication being dispensed. Elongated slits and other alternative aperture shapes are suggested.

As the medicament being administered moves directly through the exterior wall from an individual conduit in this channel balloon, jetting from the single apertures can still occur. Moreover, forming apertures in the outer wall is more complicated in a channel balloon that it is in a concentric balloon structure. For example, with individual concentric balloons it is possible to laser drill holes through one balloon as an outer balloon while it is separated from the final catheter assembly and then to overlay the outer balloon on the inner balloon. With conventional laser drilling, the laser is energized for an interval that assures complete penetration of the material being drilled. In a channel balloon, however, that approach to laser drilling would require sophisticated controls designed to produce just sufficient energy during a single application of laser energy to drill the exterior wall without significantly penetrating or weakening of the inner wall. Otherwise the structural integrity of the entire channel balloon can be compromised. Instead, these single ports are formed by incremental pulsing of a laser beam so it removes only a portion of the exterior wall. As each laser pulse interacts with the exterior wall, reflections at the walls tend to produce uneven energy distributions across the hole being drilled. This process can form tabs of material that are weakly connected to the channel balloon. There is always a potential for such material to release and form debris that can block the channel or, in the worst case, exit with the medication into the patient. These and other criteria would require the implementation of complicated and unduly expensive manufacturing controls to adapt prior art procedures for avoiding jetting to an extruded channel balloon.

SUMMARY

Therefore, it is on object of this invention to provide an improved inflatable medical device for the intravascular delivery of medications.

Another object of this invention is to provide an improved inflatable medical device that minimizes jetting effects during the administration of a medication.

Still another object of this invention is to provide an improved inflatable medical device for the intravascular delivery of medication at high flow rates without jetting effects.

Yet another object of this invention is to provide an improved inflatable medical device for the intravascular delivery of medications with a channeled expansible balloon.

Yet still another object of this invention is to provide an improved inflatable, channeled balloon catheter for the administration of medication that is readily manufactured.

Still yet another object of this invention is to provide an improved, reliable and inflatable, channeled balloon catheter medical device for the intravascular delivery of medications.

In accordance with one aspect of this invention, a medical device for the intravascular delivery of medications includes an inflatable balloon having at least one conduit that extends between interior and exterior walls for substantially the entire length of the balloon. Lumens are provided for inflating the balloon and for delivering medications to the conduit. An array of closely spaced ports through the exterior wall are grouped in an area that is significantly less than the area of the exterior wall coextensive with the conduit thereby to enable medication to exit the conduit.

In accordance with another aspect of this invention, a medical device for the delivery of medications includes a multi-lumen catheter having a distal end adapted to be disposed within a bodily organ. A hollow, inflatable, balloon defined by interior and exterior walls and distal and proximal ends is disposed on the distal end of the catheter. The interior of the balloon is in fluid flow relationship with one lumen to enable the introduction of an inflation fluid to the interior of the balloon. A plurality of conduits formed intermediate the interior and exterior walls receive medications. The exterior wall of each conduit has a given exterior wall area. Each conduit is adapted to receive medications through another lumen and includes an array of closely spaced ports through the exterior wall. Each array covers an area that is significantly less than the exterior wall area over the conduit.

In accordance with another aspect of this invention an inflatable medical device for the delivery of medications to an organ in the body includes a hollow, inflatable, medication-deliverable balloon defined by interior and exterior walls. The exterior wall contains an array of closely spaced ports constructed by positioning an optical mask proximate the exterior wall. The optical mask includes a plurality of apertures therethrough that correspond to the desired array. Laser pulses are directed toward the optical mask with the energy in a single pulse limited to a level that removes only an incremental portion of the exterior wall material. The pulse energy is spread to illuminate all the apertures in the mask simultaneously. The process is monitored until the presence of laser energy on the inner wall is detected whereupon the sequence of laser pulses terminates.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
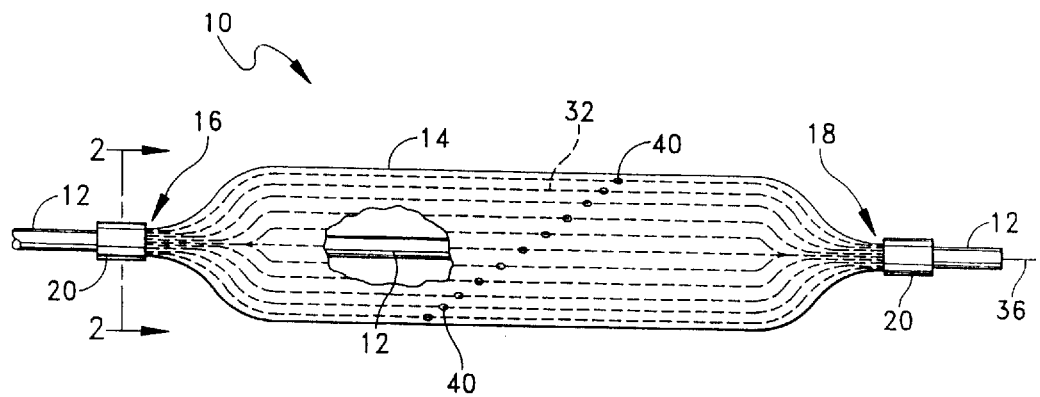
FIG. 1 is a side elevational view of a medical balloon according to the present invention shown in an inflated configuration with a portion of balloon being cut away to show its interior.

A balloon-type catheter 10 of the present invention is similar to other catheters used for treating coronary artery disease. As is conventional, the catheter 10 attaches to an array of hubs (not shown) being typically made of rigid materials. These hubs enable the introduction of inflation fluids, medication and a guide wire as will be described hereinafter. The hubs attach to the proximal end of a multilumenal tube or catheter shaft 12 as is conventional.

The catheter shaft 12 carries a medical balloon 14 at its distal end. The balloon 14 comprises materials described herein and is heat sealed or adhesively attached (as is conventional) at its respective proximal end 16 and distal end 18 to the catheter shaft 12. A collar 20 fits around the proximal end 16 of the balloon 14; an optional collar may be attached to the distal end 18. An inflation port (not shown) provides communication between the interior of the balloon 14 and an inflation lumen 24, as also known in the art. Lumen 24 communicates with any desired source of inflation fluid at the hubs mentioned above as is conventional for balloon catheters.

The medication lumen 26 extends completely through the catheter shaft 12 and communicates with a medication injection port 28 at the proximal end 16 of the balloon 14.

The medication injection port 28 communicates with a manifold 30 that is formed between the collar 20 and the catheter shaft 12 and that is in fluid flow communication with medication dispensing conduits 32.

A third lumen 34 extends completely through the catheter shaft 12. This lumen 34 allows a conventional guidewire 36 to be inserted through the balloon 14 to assist in catheter insertion in a conventional manner.

Figure 3:
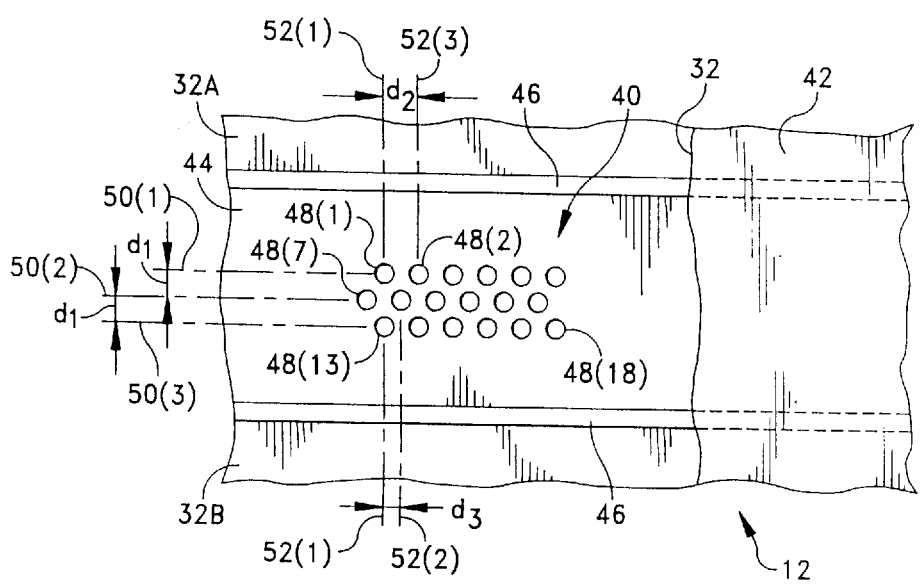
FIG. 3 is an enlarged plan view of a portion of the balloon in FIG. 1 that includes one conduit and portions of adjacent conduits.
Figure 4:
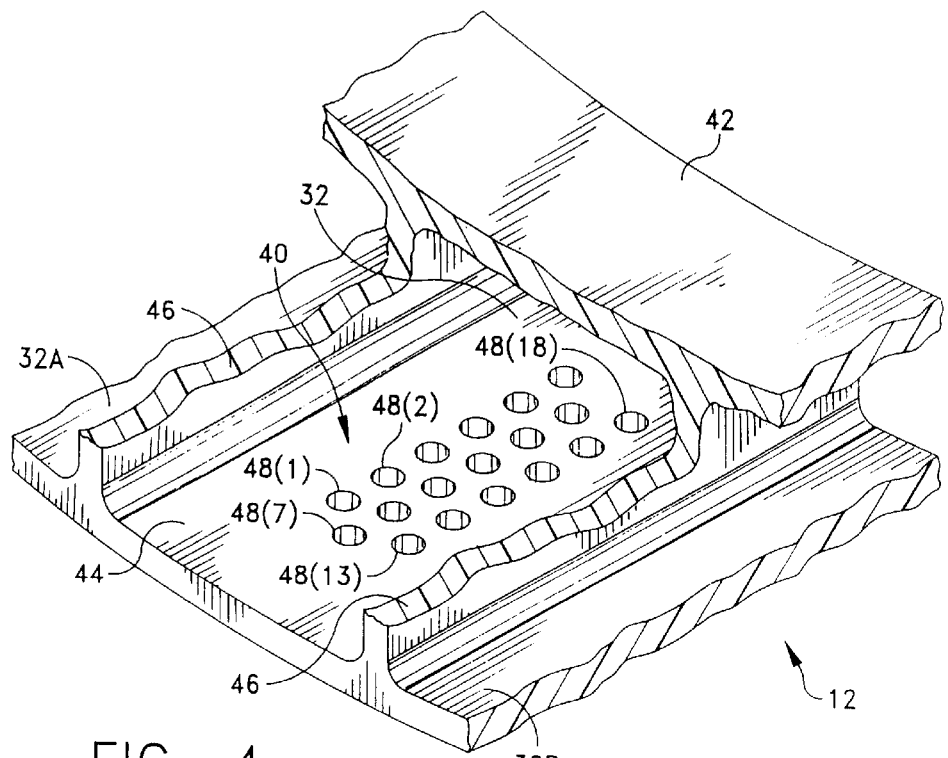
FIG. 4 depicts the portion of the balloon shown in FIG. 3 in perspective.

FIGS. 3 and 4 depict a portion of a balloon 14 that forms one conduit 32 and portions of adjacent conduits 32A and 32B and that, as shown in FIGS. 1, 3 and 4, includes an array 40 of apertures or ports for dispensing medication. Still referring to FIGS. 3 and 4, the balloon 14 includes an inner cylindrical expansible wall 42 and an outer expansible wall 44 spaced from the inner wall 42 by radially extending webs 46.

The array 40 of apertures includes, in this specific embodiment an array of eighteen ports 48(1) through 48(18) organized in three rows centered on parallel axes 50(1), 50(2), 50(3) that parallel the webs 46. The apertures 48 additionally are arranged in offsetting columns. For example, ports 48(1) and 48(13) are at the intersections of a center line 52(1) with center lines 50(1) and 50(3), respectively. Ports along the axis 50(2), such as port 48(7), are offset and lie on a center line 52(2) parallel to center lines 52(1) and 52(3) and midway therebetween. If $d_1$ represents the distance between adjacent ones of the axes 50; $d_2$, the distance between the center lines of adjacent ports along an axis such as the distance between center line 52(1) and 53(3); and $d_3$, half the distance of $d_2$, spacing for maintaining the integrity of the material intermediate adjacent ports can be realized so long as $$d_1 \geq 2d$$

$$d_2 \geq 2d$$

$$d_3 \geq d$$

where "d" is the nominal diameter of an individual one of the ports 48. If the ports 48 have a diameter of 30 μm, according to equations (1) through (3) the array 40 occupies an area of about 150 μm by 330 μm. In one particular embodiment the distance $d_2$ is increased over the minimum and the array 40 has an area of 160 μm by 450 μm whereby the minimum spacing between adjacent ports in any direction is equal to or greater than the port diameter, d. Thus, the ports 48 constitute a two-dimensional array of closely spaced ports.

The production of a balloon 14 as shown in FIGS. 3 and 4 with an array 40 can be accomplished with the specifically disclosed pattern shown in FIGS. 3 and 4 or with any alternate configuration. The number of ports 48 can be varied. In accordance with certain objectives of this invention, however, in whatever form, this structure allows medication transmitted throughout the conduit 32 to ooze from the ports 48 collectively. Given the close proximity of the apertures 48 and their small sizes, the individual ports seem to act more like capillaries than nozzles, so the medication streams or jets observable in the prior art do not appear. This jetting is overcome without adding materials to the balloon or constructing a balloon with inner and outer ports that necessitates the use of an inflation fluid, the removal of an inflation fluid and the subsequent introduction of an additional fluid for the purposes of inflating the balloon and thereafter administering the medicine, with its obvious complexity and disadvantages.

Figure 5:
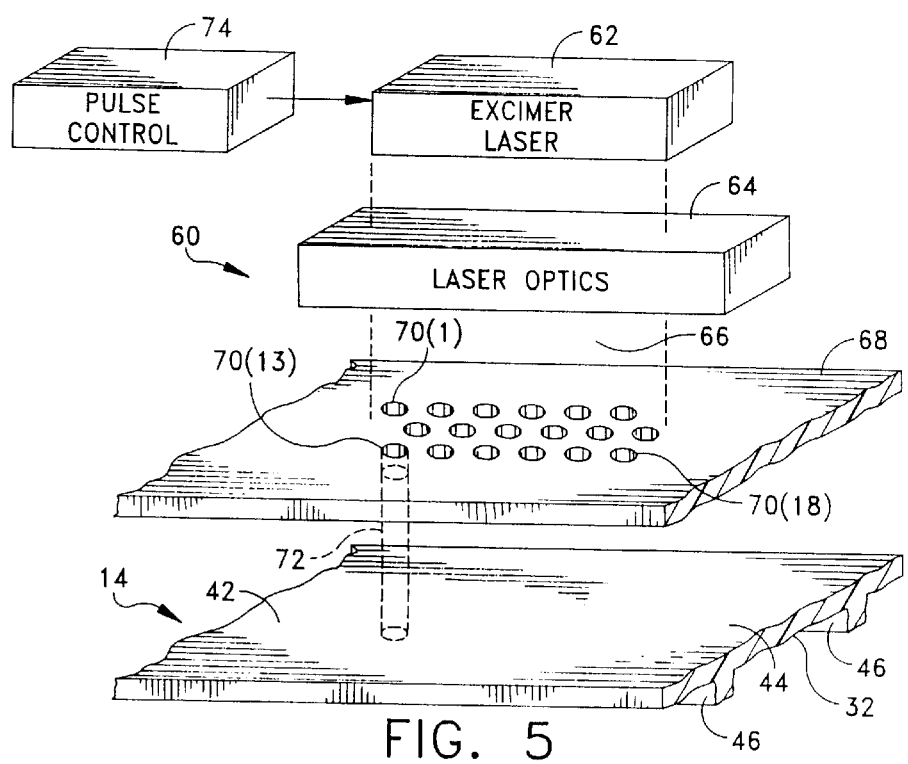
FIG. 5 depicts, schematically and in block form, apparatus useful in the manufacture of a balloon constructed in accordance with this invention.

FIG. 5 schematically depicts manufacturing apparatus 60 that is useful in forming the array 40. In one particular embodiment, an excimer laser 62 and conventional laser optics 64 form a laser beam having boundaries represented by dashed lines 66 and that covers an area corresponding to at least the area of the array to be formed. As previously indicated, an array generally will cover an area less than 1 mm² (i.e. less than 1000 μm on each side). With such areas optics 64 can produce a substantially even energy distribution across the area of the array. The methods for producing a laser pulse having these characteristics and a sequence of such pulses is well known in the art.

An optical mask 68 includes a plurality of apertures, such as apertures 70(1) through 70(18), that correspond to the array 40. After the mask 68 is interposed between the laser optics and the exterior wall 44, laser energy from the optics 64 strikes the mask 68, but passes through the mask 68 only in the areas corresponding to each of the various apertures 70 in the mask. Consequently the laser optics 64 and mask 68 will illuminate the exterior wall 44 with laser energy in the desired pattern. Dashed lines 72 depict the transfer of energy through the aperture 70(13) to the exterior wall 44.

The apparatus 60 additionally includes a pulse control circuit 74 that establishes laser parameters of pulse amplitude, width and repetition to enable the laser 62 to illuminate the mask 68 with a sequence of controlled finite energy pulses. More specifically, it is desired to control pulse amplitude and width so each pulse removes only an incremental portion of the material in the exterior wall 44. If the balloon 14 is extruded from polyethylene terapthalate or similar material, the pulse control circuit 74 may limit each laser pulses to an energy of 1 millijoule, such that it requires 20 to 25 pulses penetrate the exterior wall 44.

Figure 6A:
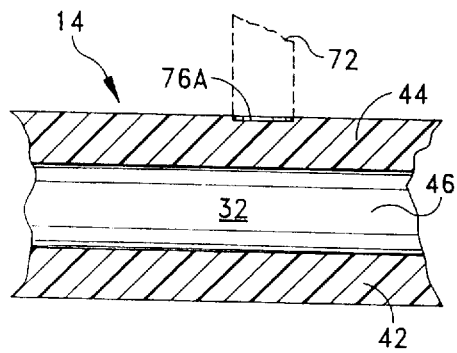
FIGS. 6A through 6D depict the formation of a single aperture through an exterior wall of the balloon during manufacture on the apparatus shown in FIG. 5.
Figure 6B:
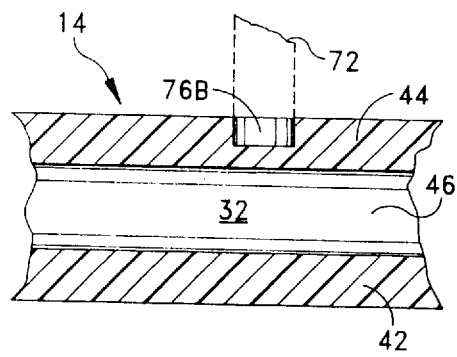
Figure 6C:
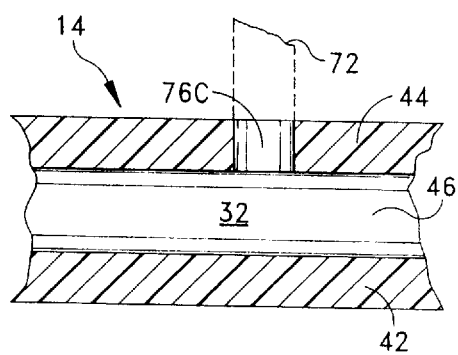
Figure 6D:
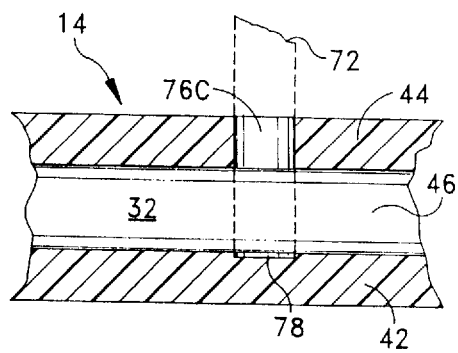

FIGS. 6A through 6D depict the progressive removal of one aperture through the exterior wall 44 under the application of a series of laser pulses. FIG. 5A represents the balloon 14 after the laser beam 72 has been pulsed one or two times and depicts a slight depression 76A made by the removal of a first incremental portion of the material of the exterior wall 44. Successive pulses deepen the hole as shown in FIG. 6B by the depression 76B in the exterior wall 44. After a number of pulses, the laser will remove all the material in the exterior wall 44 as shown in FIG. 6C. A next laser pulse passes through the aperture 76C shown in FIG. 6D and strikes the interior wall 42. In essence, the materials in the walls 42 and 44 generally are opaque or semi-opaque so an operator can visually determine when an aperture such as aperture 76 is fully formed by the appearance of a surface irregularity on the interior wall 42. At that point the operator stops the laser pulse sequence.

Normally, the laser pulse control 74 may be as simple as a manually activated single-pulse circuit so each pulse is controlled individually. Alternatively, the manual control might initiate a short pulse train of 2 or more pulses in a burst. Typically this control would be designed so that only one or two pulses would be generated after the hole 76C is fully formed. These pulses may form a surface irregularity 78 on the inner wall 42. However, the incremental material that is actually removed does not affect the overall strength or integrity of the inner wall 42.

Figure 2:
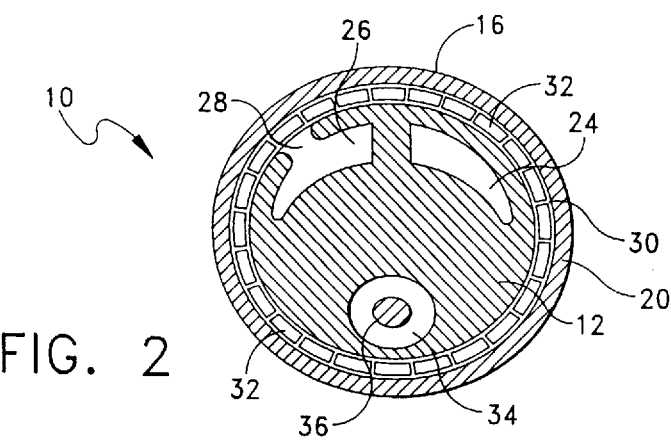
FIG. 2 is cross section taken along lines 2—2 in FIG. 1 showing the attachment between the catheter shaft and the balloon.

Mechanically forming apertures such as apertures 48 in FIG. 2 by pricking or otherwise can produce flashing around the hole. Even a tightly focused laser beam for drilling a single hole can produce flashing around the peripheral edges because there can be a significant variation in energy distribution across the diameter of the hole. Such flashing is difficult to remove, particularly in a channel balloon, and it is possible for such flashing to detach during use. The laser optics 64 in FIG. 5 spreads the resulting laser beam over the array and assures a relatively constant energy distribution across portions of the beam passing through the optical mask 68 that is in a single laser beam represented by the dashed line 72. As the energy in each beam from the mask 68 will be substantially constant, each hole 48 tends to form at equal rates through the exterior wall 46 so that within one or two pulses all the holes will be bored at the same time. This minimizes any damage by laser energy impacting the interior wall 42.

Moreover, as compared with the prior art, the combination of the use of the mask to form an array of small holes, rather than a single hole also minimizes the size of any tabs or flash that remain after forming the holes. Whereas such tabs or flashing in prior art sufficiently large to produce problems if they were to migrate into a patient, with the process of this invention any flashing or tabs that might be produced are of negligble size and quantity.

As will now be appreciated, conventional laser drilling is not adapted for producing an array in a channel balloon. Laser pulse width and amplitude are selected to form a port with one pulse. Any variation in the energy from port to port could produce an array with fully formed and partially formed apertures. A successive pulse, without other controls, would pass through any fully formed holes and damage the interior wall. The use of differential or incremental energy pulses in accordance with this invention overcomes this problem because the energy applied at a location in the array during each pulse is substantially constant and because the energy in any one pulse is insufficient to penetrate fully the exterior or interior wall.

Thus a balloon catheter structured in accordance with this invention meets the several objectives of this invention. Specifically, the apparatus and method of operation as shown and described with respect to FIGS. 5 and 6A through 6D provide reliable and straightforward balloon production with controlled aperture arrays in the exterior walls of each conduit in a channel balloon. The process is readily adapted for forming multiple arrays, although individual arrays in any given conduit will be separated. Moreover, each array will have an overall area that is insignificant with respect to the total area of the exterior wall portion corresponding to a given conduit. Finally, the array of closely spaced holes minimizes jetting encountered in prior art medication delivering balloons without the requirement of additional structures or special materials.

This invention has been disclosed in terms of certain embodiments. It will be apparent that many modifications can be made to the disclosed apparatus without departing from the invention. For example, an array can take any shape and spacing provided the spacing between adjacent ports is sufficient to maintain the integrity of the exterior wall between those ports. Typically that requires a spacing by the diameter of the aperture or greater. Likewise the number of holes can be varied in the array. Moreover, arrays can be formed in the exterior walls of all the conduits or in only selected ones of the conduits. The process can also be used to form apertures in balloons of a conventional concentric form as well as channel balloons. Therefore, it is the intent of the appended claims to cover all such variations and modifications as come within the true spirit and scope of this invention.

What is claimed as new and desired to be secured by letters patent of the United States is:

1. A medication delivery device including a hollow, inflatable, balloon defined by interior and exterior balloon walls and spaced ribs extending between the interior and exterior balloon walls for defining a plurality of elongated discrete parallel channels between the balloon walls for receiving the medications, the improvement of a port position at each exterior wall of each channel, each port position consisting of a two-dimensional array of closely spaced ports through the exterior wall, in which area of the array is significantly less than the area of the exterior wall coextensive with the channel, said two-dimensional array being constructed by A. positioning an optical mask proximate the exterior wall at one channel at a location for the array said optical mask having a plurality of apertures therethrough that correspond to the two-dimensional array, B. directing a sequence of laser pulses toward said optical mask thereby to enable energy in each laser pulse to pass through the apertures, the energy of each laser pulse being maintained to remove only an incremental portion of the exterior wall in register with each aperture, and C. monitoring the interior wall to determine the impingement of laser energy thereon thereby to terminate the sequence of laser pulses.

2. A medication delivery device as recited in claim 1 wherein the laser energy is supplied from an excimer laser and the energy in each pulse is about one millijoule.

3. A medication delivery device as recited in claim 2 wherein said sequence includes less than 25 laser pulses.

4. A medication delivery device as recited in claim 3 wherein said sequence includes a number of pulses in the range from 10 to 20 and the apertures through said optical mask have a diameter that produces a port having a diameter of about 30 microns.

* * * * *